US00PP29949P2

(12) United States Plant Patent
Hansen

(10) Patent No.: US PP29,949 P2
(45) Date of Patent: Dec. 4, 2018

(54) **X *MANGAVE* PLANT NAMED 'PURPLE PEOPLE EATER'**

(50) Latin Name: ***x Mangave* times *Agave***
Varietal Denomination: Purple People Eater

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/732,275

(22) Filed: Oct. 17, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt

(57) ABSTRACT

A new and unique X *Mangave* plant named 'Purple People Eater' characterized by long, broad, slightly arching, glaucous greenish-purple foliage, that develop reddish-purple spots densely covering the upper and lower surfaces especially with high ultraviolet light exposure. Leaves have medium-sized semi-flexible marginal spines and semi-flexible apical spine. Growth rate is moderate. The new plant is suitable for the garden or as a potted plant in the garden or home.

1 Drawing Sheet

Botanical classification: hybrid; x *Mangave* times *Agave*.
Variety denomination: 'Purple People Eater'.

BACKGROUND OF THE INVENTION

The present invention relates to the new and distinct X *Mangave* hybrid plant, X *Mangave* 'Purple People Eater' hybridized by the inventor at a wholesale perennial nursery in Zeeland, Mich., USA as cross between a X *Mangave* 'Bloodspot' (not patented) as the female or seed parent times a selection of *Agave gypsophila* (not patented) as the male or pollen parent. The cross was performed on Dec. 26, 2011 and seeds were harvested Apr. 1, 2012 and sown on Aug. 8, 2012. After passing trials at the same nursery the plant was assigned the breeder code XMANG-12-03-25. The new plant has been successfully asexually propagated initially by division at the same nursery in Zeeland, Mich. and also by sterile shoot-tip tissue culture. Both methods of asexual propagation systems have been found to produce stable and identical plants that maintain all the unique characteristics of the original plant.

No plants of X *Mangave* 'Purple People Eater' have been sold, under this or any name, in this country or anywhere in the world, prior to the filing of this application, nor has any disclosure of the new plant been made prior to the filing of this application with the exception of that which was disclosed or sold within one year of the filing of this application, and was either derived directly or indirectly from the inventor.

BRIEF SUMMARY OF THE INVENTION

X *Mangave* 'Purple People Eater' differs from its parents as well as all other *Manfreda, Agave* and X *Mangave* known to the inventor. The most similar cultivars known to the inventor are X *Mangave* 'Lavender Lady' U.S. Plant Pat. No. 29,194, X *Mangave* 'Silver Fox' U.S. Plant Pat. No. 29,642 and X *Mangave* 'Tooth Fairy' U.S. Plant Pat. No. 29,599. Compared with the female parent the new plant has broader more concaved foliage of glaucous greenish-purple with smaller spotting. Compared with the male parent the new plant is more compact with shorter, less curled and more reddish-purple spotted foliage with smaller and more flexible marginal spines. Compared with 'Lavender Lady' the new plant has larger leaves more distinctly spotted reddish-purple. Compared with 'Silver Fox' the new plant has longer leaves that have more distinctly spotted reddish-purple coloration and smaller marginal spines. Compared with 'Tooth Fairy' the new plant has more curved foliage with smaller marginal spines and more distinctly spotted reddish-purple coloration.

The new plant, 'Purple People Eater', is unique from all of the above cultivars and all *Agave*, X *Mangave* and *Manfreda* known to the inventor by the following combined traits:

1. Long, broad, slightly arching, slightly-folded, foliage of glaucous greenish-purple;
2. Leaves develop small spots of frequently overlapping reddish-purple spots densely covering throughout upper and lower surfaces;
3. Medium-sized, semi-flexible spines on leaf margins and semi-flexible apical spine of greyed-orange;
4. Moderate growth rate.

BRIEF DESCRIPTION OF THE DRAWING

The photographs of x *Mangave* 'Purple People Eater'; demonstrates the overall appearance of the new plant including the unique traits as a three-year-old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
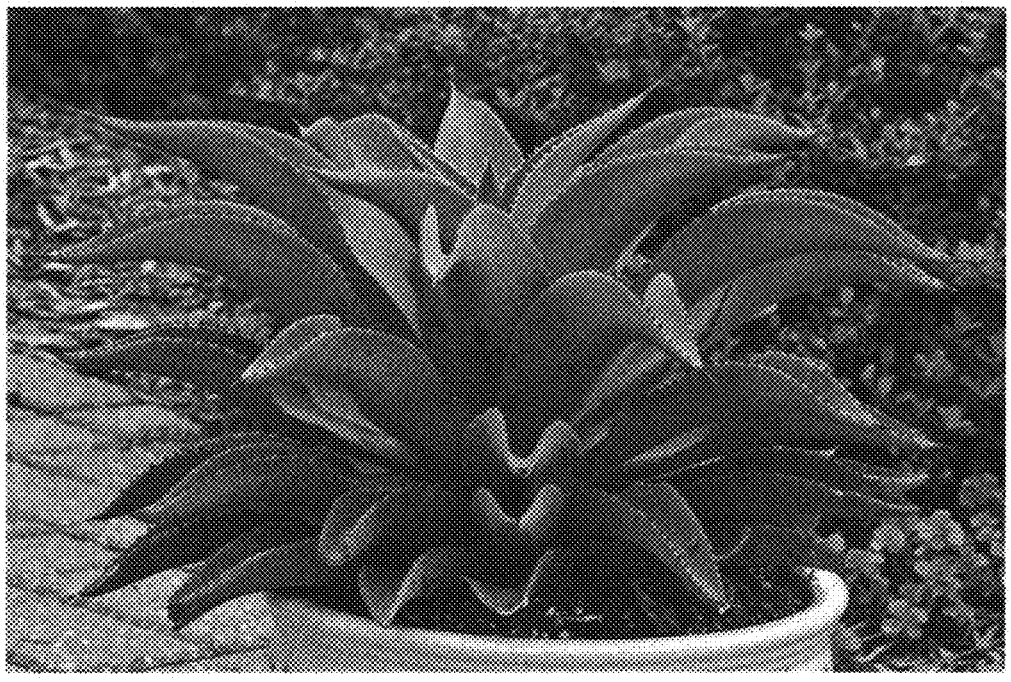
FIG. 1 shows the new plant having been grown in a container.
Figure 2:
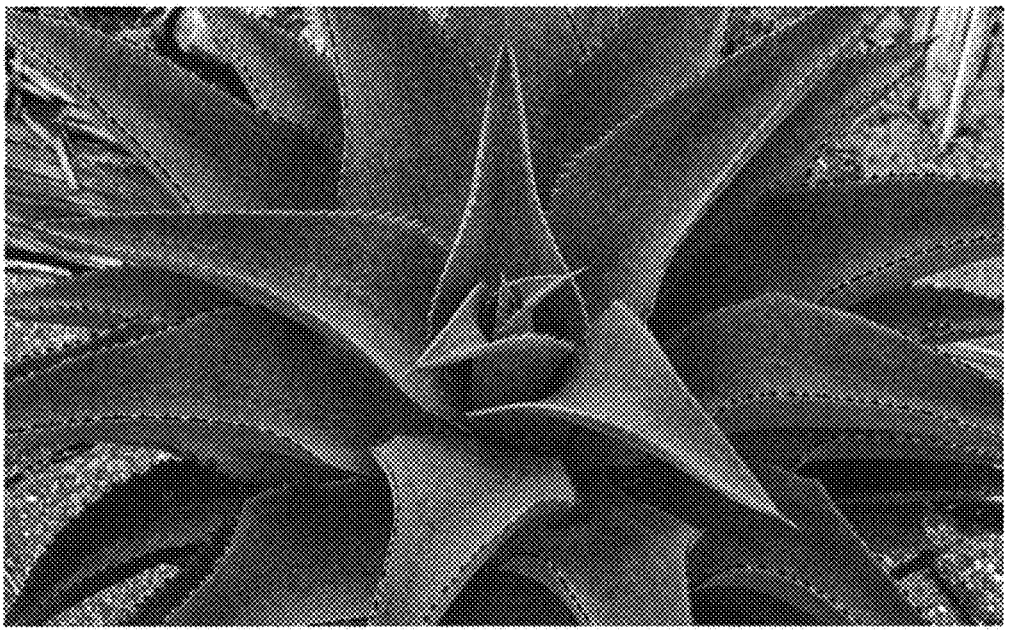
FIG. 2 shows a close-up of the slightly folded foliage with dense spots and marginal leave spines.

The following descriptions and color references are based on the 2015 edition of The Royal Horticultural Society Colour Chart except where common dictionary terms are used. The new plant, X *Mangave* 'Purple People Eater', has not been observed under all possible environments. The phenotype may vary slightly with different environmental conditions, such as temperature, light, fertility, moisture and maturity levels, but without any change in the genotype. The following observations and size descriptions are of a two-year-old plant in a commercial wholesale greenhouse and three-year-old plant in container in Zeeland, Mich. with supplemental water and fertilizer as needed.

Parentage: The female or seed parent is X *Mangave* 'Bloodspot' (not patented); the male or pollen parent is a selection of *Agave gypsophylla* (not patented);

Propagation: Division of side shoots and sterile shoot-tip tissue culture;

Time to initiate roots from tissue culture: About 21 days;

Growth rate: Moderate;

Crop time: About 14 to 16 weeks to finish in a 3.8 liter container from a 35 mm tissue culture growing at about 21° C.;

Rooting habit: Fleshy, lightly branching, with roots 20 to 30 cm long;

Root color: Nearest RHS NN155A when active;

Plant shape and habit: Succulent herbaceous perennial with basal rosettes of about 84 leaves radially emerging from center crown and slightly arching from central rhizome, with lower leaves extending slightly below the soil line when grown in containers, producing a radially-symmetrical, rounded mound;

Plant size: Foliage height about 32.0 cm tall from soil line to the top of the leaves and about 48.0 cm wide at the widest point below soil line in container;

Foliage description: Lanceolate; simple; margins dentate; slightly concavo-convex; apex narrowly acute with semi-flexible spine; base truncate, sessile; bi-laterally symmetrical; densely covered with frequently overlapping reddish-purple spots between 0.5 mm and 7.0 mm diameter, average about 3.0 mm diameter; glaucous both surfaces;

Leaf size: To about 24.5 cm long, about 7.0 cm wide at base and about 2.5 mm thick at midrib; average about 22.0 cm long, about 5.5 cm wide and about 4.5 mm thick at midrib base; apical spines to about 5.0 mm long and 4.0 mm across at midrib base;

Marginal spines: Narrowly acute; about 2.0 mm long; average about 2.0 mm apart;

Foliage fragrance: None observed;

Leaf blade color: Becoming more glaucous and more thickly spotted with reddish purple in higher ultraviolet light exposure;

*Adaxial* (*young*).—Blend of between RHS N138D and RHS 138B with spots of nearest RHS 59 B at base and N186C distally; Abaxial (young): blend nearest RHS 138B with spots blend between RHS N187A and RHS 187B.

*Adaxial* (*mature*).—Blend between RHS N138B and RHS N187B with spots RHS N187B and RHS 187B; Abaxial (mature): nearest RHS 138B and with spots between RHS N187A and RHS N186C.

*Marginal spines*.—Color (young) nearest RHS 160B; (mature) nearest RHS 175A.

Apical spine: Becoming dry and semi-flexible, entire; about 18.0 mm long and 2.0 mm across at base; color on young leaves nearest RHS 172A at apex and nearest RHS 161A at base, at maturity nearest RHS 200B;

Petiole: Sessile;

*Veins*.—Parallel; not distinct abaxial or adaxial no color variation between other leaf tissue.

Flower description: Not yet observed;

Fruit and seed: Not yet observed;

Disease resistance: X *Mangave* 'Purple People Eater' has not been observed to be resistant to diseases beyond that which is normal for X *Mangave, Agave* or *Manfreda*. The plant is xeromorphic and survives well with minimal water once established. The new plant is hardy at least from USDA zone 8b to 11. Full extent of winter hardiness has not been tested.

It is claimed:

1. A new and distinct cultivar of ornamental X *Mangave* plant named 'Purple People Eater' as herein described and illustrated.

* * * * *